United States Patent [19]

Quenin et al.

[11] Patent Number: 5,026,526

[45] Date of Patent: Jun. 25, 1991

[54] AUTOMATED CAPPING MEANS FOR ANALYZER PIPETTE

[75] Inventors: John A. Quenin, Rochester; Raymond F. Jakubowicz, Rush, both of N.Y.

[73] Assignee: Eastman Kodak Company, Rochester, N.Y.

[21] Appl. No.: 477,405

[22] Filed: Feb. 9, 1990

[51] Int. Cl.⁵ .......................................... G01N 35/06
[52] U.S. Cl. .................... 422/64; 422/100; 422/104; 422/82.05; 436/46; 436/45; 73/864.01
[58] Field of Search .............. 422/100, 104, 64, 82.05; 436/46, 45; 73/864.01

[56] References Cited

U.S. PATENT DOCUMENTS 4,059,020 11/1977 Avakian ........................ 73/863.25
4,943,415 7/1990 Przybylowicz et al. ......... 422/64

FOREIGN PATENT DOCUMENTS 287005A 4/1987 European Pat. Off. ........... 436/46

Primary Examiner—David L. Lacey
Assistant Examiner—Abanti B. Singla
Attorney, Agent, or Firm—Dana M. Schmidt

[57] ABSTRACT

There is described an analyzer capping element for blocking off air access to pipette tips, such capping element being mounted for automatic unblocking directly in response to movement of a test element into position for pipette dispensing.

5 Claims, 4 Drawing Sheets

5,026,526

AUTOMATED CAPPING MEANS FOR ANALYZER PIPETTE

FIELD OF THE INVENTION

The invention relates to an analyzer for assaying body liquids, and particularly to a structure useful with a pipette mechanism used therein.

BACKGROUND OF THE INVENTION

Analyzers used to test body liquids for their concentration of analytes often use slide-like test elements. A small amount of a patient sample liquid is dispensed from a pipette onto such a test element, which is then incubated and "read" for a detectable change indicative of the concentration of analyte. Frequently, "n" dispensing steps occur from the same patient sample, onto "n" different test elements to run "n" different assays. This requires each sample at the pipette to remain at the dispensing station until all the "n" dispensing events are made. (The sample is usually contained in a disposable tip in the pipette.)

In high speed analyzers, little delay occurs between each of those "n" dispensing events. However, in some newer analyzers, delays as much as 3.5 minutes can occur between sequential dispensing. An example includes those analyzers that have the detecting or "read" station located off the incubator, and which test for rate assays as well as end-point assays. Such rate assays require a single test element to remain at the detecting station for one minute or more, while as many as 95 separate readings are taken to confirm the rate of change of the signal. This means that the incubator upstream is unable to offload any other test elements. This in turn prevents new test elements from having sample liquid dispensed thereon, since there is no room in the incubator to place them. Thus, the pipette has to delay substantially, with exposed sample in the tip, until the next amount of sample can be dispensed.

A delay between sequential dispensing by the pipette is particularly significant if the patient sample has high amounts of protein, as is often the case. Without a cover placed over the exposed dispensing tip, such sample can dry up, plugging the tip to prevent the next dispensing step. Alternatively, the analyte concentration can be unacceptably altered due to sample evaporation at the tip.

Pipette tips have been covered in the past to prevent this problem. However, such constructions have involved either operator-handling of the covers (to remove them and replace them), or separate analyzer actuation in response to the operator or a signal indirectly responsive to a new test element entering the system. Separate operator intervention is undesirable as it is a source of errors and delays. Any automated operation of tip covers that is only indirect, is also subject to delays and errors due to separate action required by the analyzer.

What has been needed, prior to this invention, particularly in analyzers having significant delays between sequential dispensing of patient sample, is capping means for the pipette tips that are directly operated, that is, removed, by the presence of a test element ready for dispensing. In this way, the tip uncovering is only responsive to the direct presence of the test element to be spotted, and there is avoided the chance of error that is possible with less direct actuation or removal of the capping means.

SUMMARY OF THE INVENTION

I have constructed an analyzer that avoids the above-noted problems.

More specifically, there is provided an analyzer useful in assaying an analyte of a body liquid dispensed onto a test element, the analyzer including means for guiding a test element along a predetermined path and means adjacent the path for positioning a pipette to dispense a patient sample on a test element on a portion of the path. The analyzer is improved in that it further includes capping means for blocking air access to the dispensing end of the pipette to prevent evaporation of liquid, and means for movably mounting the capping means within the path, the mounting means being constructed to allow the capping means to move from a first position that blocks the path and covers the pipette dispensing end, to a second position that unblocks the path and uncovers the pipette dispensing end; the mounting means being further constructed to permit a test element advancing along the path to push the capping means into the second position.

Therefore, advantageous features of the invention are that air evaporation around the dispensing orifice of the liquid dispenser is decreased and plugging of the orifice is reduced, even if the dispenser is left quiescent for extended periods.

It is a further advantageous feature of the invention that the function of reduced evaporation is achieved by a capping mechanism that uncaps itself only in direct mechanical response to a test element being positioned for dispensing, and not to some less direct signal.

Other advantageous features will become apparent upon reference to the following description of the preferred embodiments when read in light of the attached drawings.

DESCRIPTION OF THE PREFERRED EMBODIMENTS

Figure 1:
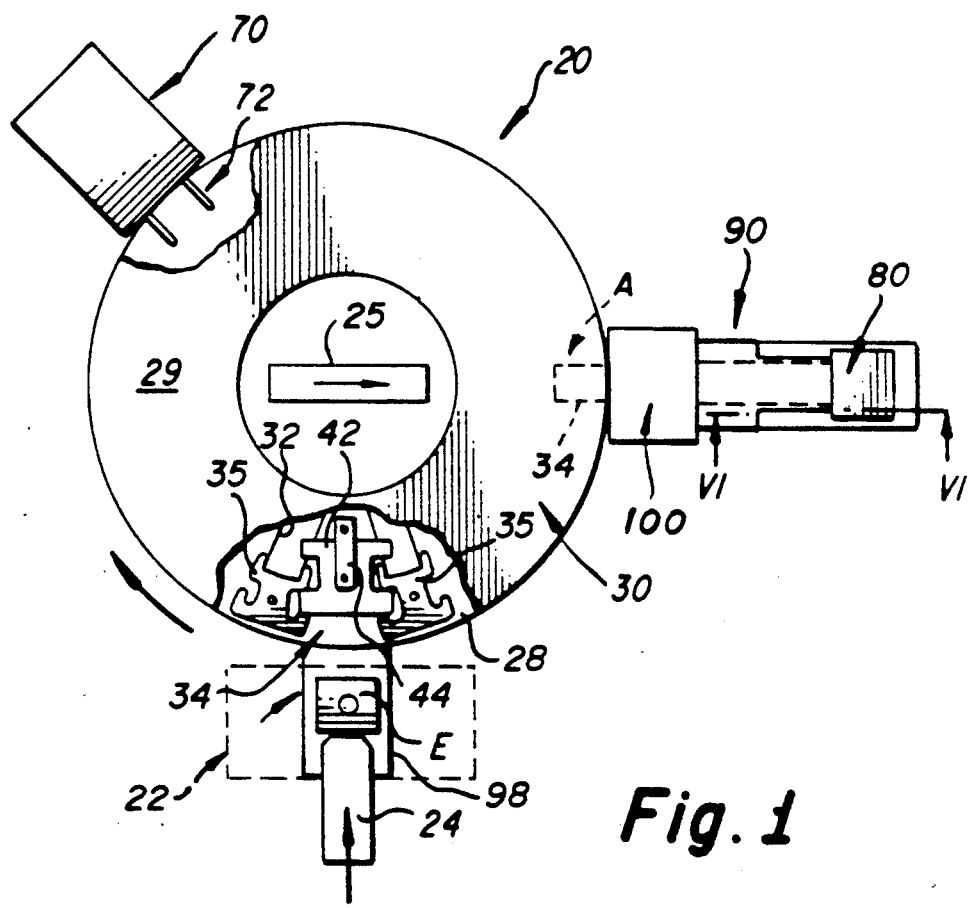
FIG. 1 is a partially schematic plan view, partially broken away, of the overall analyzer constructed in accordance with the invention.

The invention is hereinafter described in connection with the preferred embodiments, wherein the liquid dispensing station is part of an analyzer wherein the colorimetric detection is done outside of the incubator at a detection station that can take only one test element at a time, and the dispensing station features a dual pipette. Further, it is described for use with so-called dried test elements. In addition, however, the invention is useful regardless of the type of pipette used, whether liquid is dispensed onto a dried element or into cuvettes, and regardless of the stations, if any, that are downstream from the dispensing station, so long as there is a need to decrease evaporation that occurs at the orifice of the dispensing apparatus.

Orientations such as "up", "down" or "vertical" refer to those pertinent to intended uses as shown in the drawings, and are arbitrary if applied to use in a zero-g environment.

Referring to FIG. 1, an analyzer 20 constructed in accord with the invention comprises a sample-dispensing station 22, an incubator 30, means 24 for transferring test element E containing patient sample from station 22 into the incubator, a potentiometric read station 70 disposed adjacent to one side of incubator 30, a colorimetric read station 100 also disposed adjacent to the incubator and displaced circumferentially from read station 70, a container 80 to receive used test elements, and a guide 90 to direct such used test elements from read station 100 to container 80. Most preferably, transfer means 24 is a pusher blade activated and guided in a conventional manner by motors, etc., not shown, moved over a shuttle 98. Any suitable means can be used to transfer test elements E out of incubator 30 into station 100, for example, pusher blade 25.

Considering first the stations downstream from station 22, as described in the commonly-owned application U.S. Ser. No. 293,718 filed by Hans Porte on Jan. 5, 1989 entitled "Incubator and Analyzer with Improved Cap Raising Means", incubator 30 preferably features a stationary lower support plate 28 and a stationary upper cover plate 29. Either or both of these plates are heated in a conventional manner, with sensors, not shown, to provide feedback to control the incubator temperature as desired. Mounted between plates 28 and 29 is a rotor 32 providing individual test-element holding stations formed as pockets in the rotor. More specifically, indentations 34 are formed in rotor 32, and hold-down leaf springs 35 are attached along the periphery of each indentation. The indentations are shaped and sized to hold a test element E therein, and springs 35 are shaped to press a test element against lower support plate 28. Preferably, springs 34 are dual springs that extend over the top of rotor 32, with a pair of fingers adjacent each indentation. Additionally, an evaporation cap 42 is provided that is attached via a leaf spring 44 to rotor 32 to permit limited vertical movement of cap 42. Spring 44 is attached to rotor 32 and presses on cap 42. Cap 42 is raised when element E is pushed in by blade 24, by a suitable mechanism.

Regarding potentiometric read station 70, FIG. 1, such station is conventional, and features a pair of electrodes 72 that raises and lowers into contact with appropriate parts of ion selective electrode (ISE) test elements held by rotor 32. That station is not activated until an ISE test element is positioned thereunder, ready for reading, as controlled by a suitable microprocessor, not shown. (Detection of which kind of test element is at which indentation 34 is done using a bar code reader at station 22, not shown).

With respect to container 80, any suitable container can be used to collect used test elements. Preferably, guide 90 is such as to keep such test elements constrained as they are pushed into the container, as described hereinafter, particularly if the analyzer is used in zero gravity environments.

Station 100 is the station that incorporates at least the colorimetric read station. Any read station can be used that will detect colorimetric changes in the test element.

Figure 2:
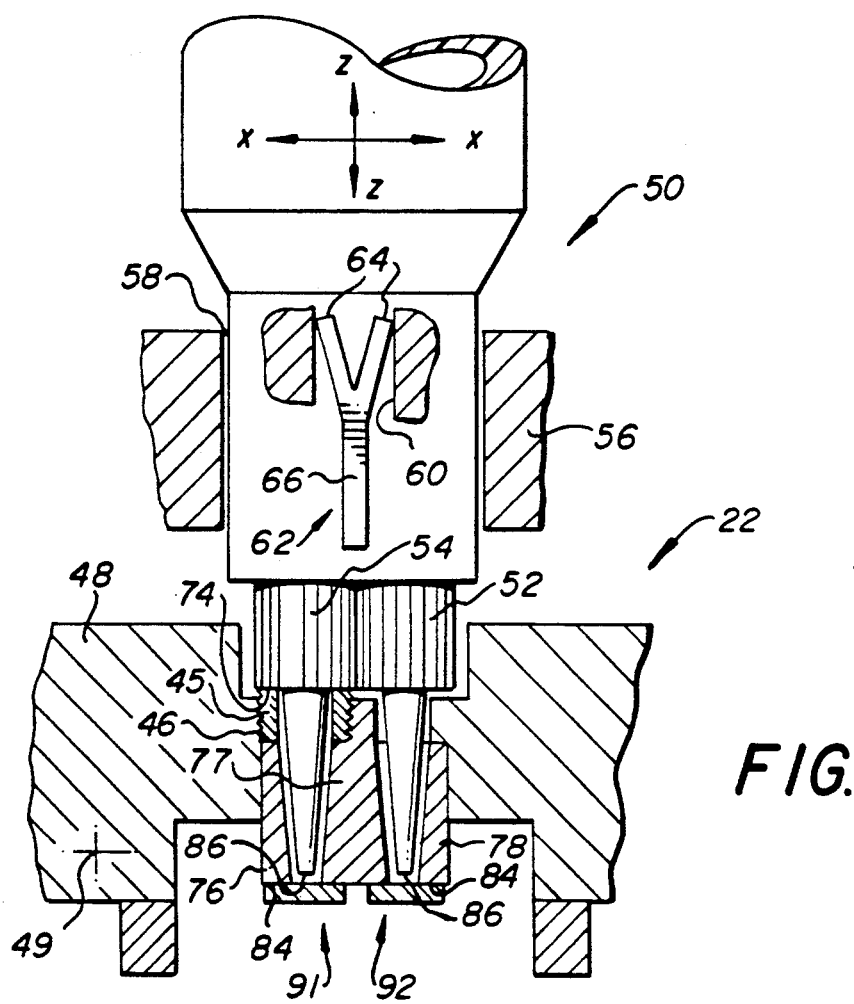
FIG. 2 is a fragmentary elevational view, partially in section, through the dispensing station showing the capping means in place relative to the pipette tips.

In accord with the invention, the dispensing of patient sample occurs at station 22, using a pipette 50, FIG. 2, here shown as a dual pipette having two disposable tips 52,54 for dispensing two different liquids. The pipette is conventional, except that it is preferably, although not necessarily, mounted in a pipette support 56 of the analyzer in an aperture 58, which has a keyway 60 that frictionally engages key 62 of pipette 50. Key 62 features a Y shape that as two spring fingers 64 biased out from support 66 that is mounted on the pipette, as described and claimed in commonly-owned U.S. Ser. No. 293,713, filed on Jan. 5, 1989, now U.S. Pat. No. 4,931,257, by J. A. Quenin and J. J. Porte, entitled "Positively Engaged Pipette and Pipette Support".

The above-noted key and keyway serve to limit the positioning of pipette 50 in the x—x and y—y direction. The vertical constraint (along the z axis) is provided preferably by a stop bushing 45 threaded into an aperture 46 so that the bushing encompasses one of the tips 54. Aperture 46 is formed in a frame member 48 that pivots for easy access about pivot point 49. Since bushing 45 can be raised or lowered by unscrewing or screwing it within aperture 46, its top surface 74 acts as the Z axis limit for the tip 54, and hence, the entire pipette 50.

To enclose the pipette tips and to help block air access to them along with the capping means described below, shrouds 76 and 78 are built into frame member 48 (either as integral parts or as parts threaded in place). As shown, shrouds 76 and 78 have a bottom surface 84 that extends below the end surface 86 of tips 52 and 54. The shrouds have a center portion 77 that is shared between them.

Figure 4:
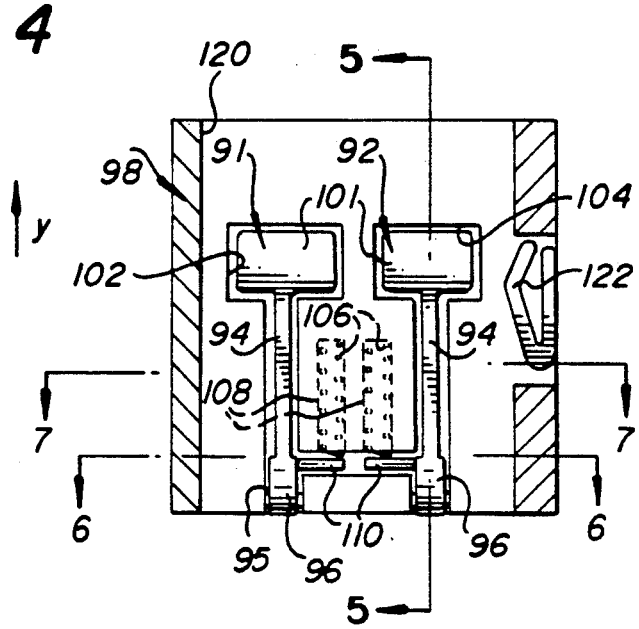
FIG. 4 is a section view taken generally along the line IV—IV of FIG. 3, to show the housing of the capping means.

To complete the blockage of air access to the tips through shrouds 76 and 78, capping means are provided, for example, in the shape of flat paddles 91 and 92, as seen especially in FIG. 4. Paddles 91 and 92 are mounted on the ends of mounting arms 94 that are pivotally attached to pivot point 95 at opposite ends 96, to the test element support shuttle 98, FIGS. 4 and 5. Pivot point 95 is located below the element support plane 97, FIG. 5, of the shuttle as set forth below. Paddles 91 and 92 are shaped with a flat contact surface 101 of sufficient surface area and flatness as to generally seal against surfaces 84 of shrouds 76 and 78, FIG. 2. This completes the sealing off of tips 52 and 54 within shrouds 76 and 78.

Figure 5:
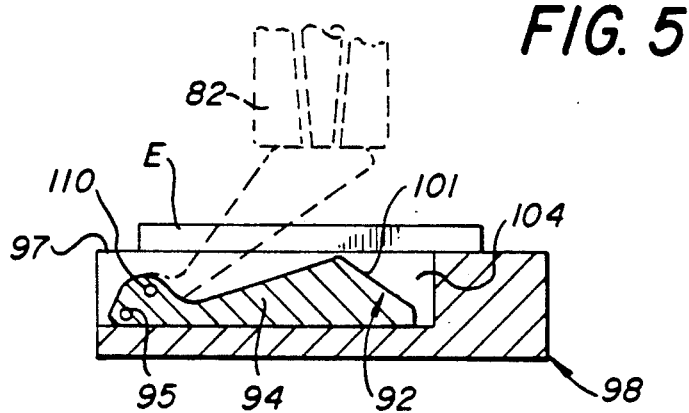
FIG. 5 is a section view taken generally along the line V—V of FIG. 4, which also shows the capping means in phantom in their raised position.

Shuttle 98 includes notches 102 and 104 shaped to accommodate paddles 91 and 92 and arms 94, when the paddles are depressed, FIGS. 4 and 5.

Figure 6:
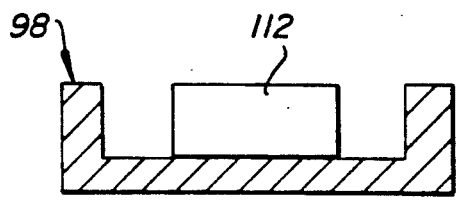
FIGS. 6 and 7 are section views taken generally along the lines VI—VI and VII—VII of FIG. 4, respectively, but without the capping means and springs, for clarity.
Figure 7:
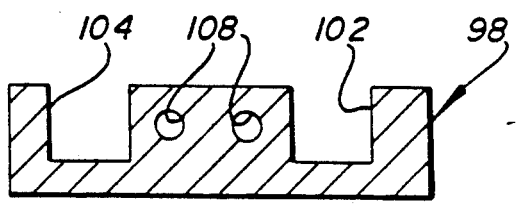

To bias mounting arms 94 upwardly so that capping paddles 91 and 92 contact the shrouds, FIG. 2, a compression spring 106 is mounted adjacent each arm notch 102 or 104, FIG. 4, in a bore hole 108, FIG. 7. Springs 106 press against a pin 110 that projects from each arm 94 adjacent ends 96, FIG. 4. The upper biased movement of paddles 91, 92 is restricted by shrouds 76, 78, or if those are not present, by shoulder 112, FIG. 6, of shuttle 98.

Figure 3:
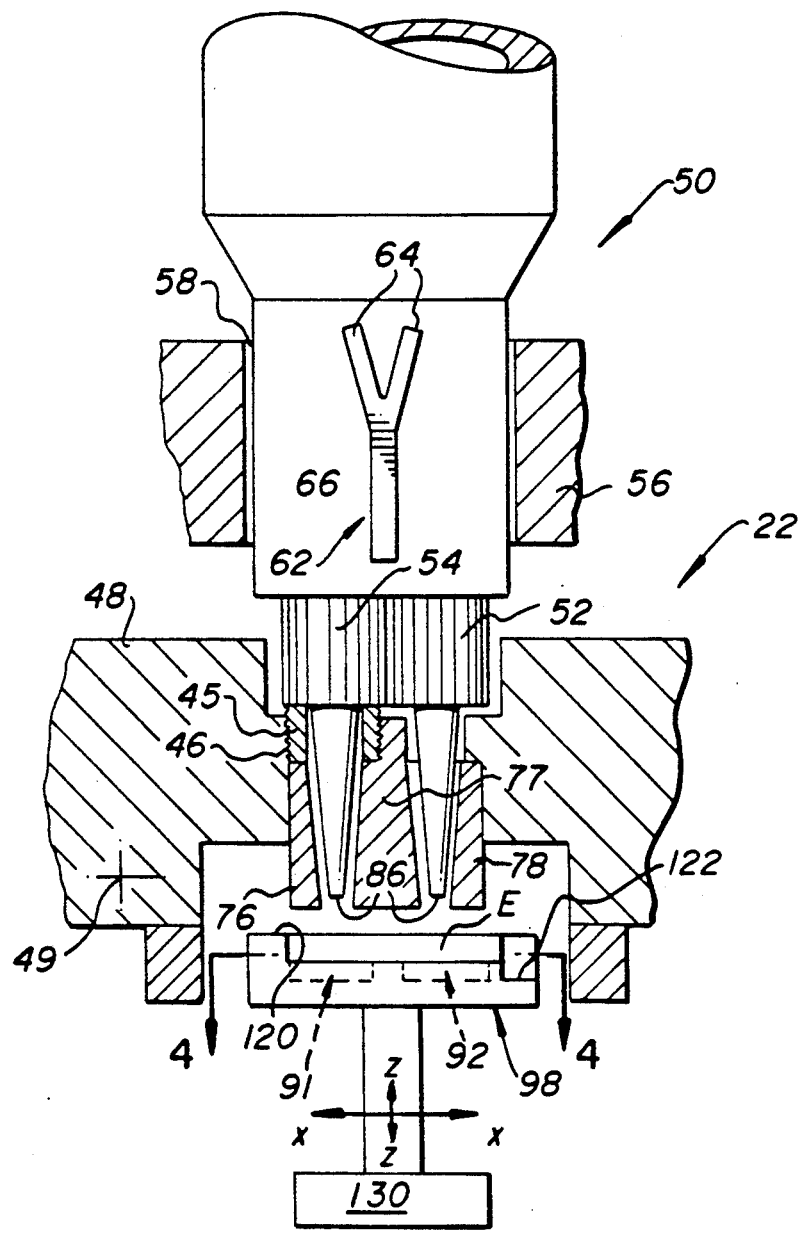
FIG. 3 is a fragmentary elevational view similar to that of FIG. 2, but showing the capping means cammed out of the way by a test element and into the test element carrier.

Support shuttle 98 is the mechanism by which a test element E, FIG. 5, is properly located in the x—x dimension, FIGS. 2 and 3, and the z or vertical dimension, FIG. 3. First. to properly locate a test element E on shuttle 98, the shuttle provides a reference shoulder 120 along one side thereof, FIGS. 3 and 4. To bias an element E against that shoulder, a spring 122 is mounted on the opposite side of the shuttle. Pusher blade 24, FIG. 1, controls how far along the y direction, FIG. 4, the element is inserted. In this fashion, an element E is fixed on the shuttle. Next, the shuttle itself preferably has freedom of movement in the x—x and the z directions. The reason is that colorimetric test elements are spotted with only one of the tips 52, 54 (FIG. 3), whereas elements E that are potentiometric are spotted by both. Furthermore, the vertical spacing (along the z axis) can be different for potentiometric elements E than it is for colorimetric elements. Any mechanism 130 that provides for such movement is useful, and does not comprise part of this invention. A particularly preferred mechanism is that described and claimed in commonly-owned U.S. application Ser. No. 293,717 filed Jan. 5, 1989 by J. A. Quenin et al entitled "Analysis Slide Positioning Apparatus and Method For A Chemical Analyzer."

Figure 8:
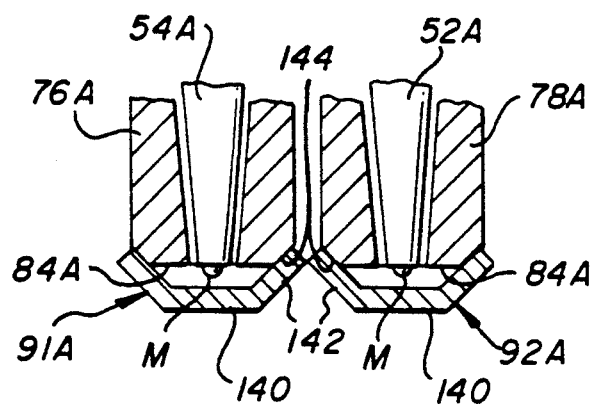
FIG. 8 is a fragmentary elevational view similar to a portion of FIG. 2, but showing an alternate form of the capping means of the invention.

It is not essential that the bottom of the shrouds extend below the tips of the pipette, provided the capping means are suitably altered as shown in FIG. 8. Parts similar to those previously described bear the same reference numeral, to which the distinguishing suffix A is appended. Thus, shrouds 76A and 78A have a bottom surface 84A that is constructed to be located generally flush with the end surface 86A of tips 52A and 54A. In such a case, because surfaces 86A are likely to have a meniscus "M" projecting therefrom, which must not contact paddles 91A and 92A lest contamination occur, those paddles are dish-shaped with a lowered center portion 140 spaced away from bottom surfaces 84A and 86A a distance sufficient to avoid contacting meniscii M. Portion 140 is then surrounded by a lip 142, and bottom surfaces 84A preferably are beveled at 144 to mate with the shape of lips 142 to seal off tip surfaces 86A from air access.

One skilled in the art will appreciate that, whichever embodiment is used, care should be taken when loading the pipette into the analyzer, to not contact support surface 74 with too much downward inertia, lest some liquid be inadvertently forced out of a pipette tip onto paddle 91 or 92, or 91A, 92A.

As a result of this invention, the uncapping step is strictly a mechanical step only, that necessarily occurs when a test element is presented for liquid dispensing. Thus, there is no need for electrical actuation of motors in response to a signal generated by a sensing means, such actuation and signal generation being a possible source of error and/or breakdown.

The invention has been described in detail with particular reference to certain preferred embodiments thereof, but it will be understood that variations and modifications can be effected within the spirit and scope of the invention.

What is claimed is:

1. In an analyzer for assaying an analyte of a body liquid dispensed onto a test element, the analyzer including means for guiding a test element along a predetermined path and means adjacent said path for positioning a pipette to dispense a patient sample on a test element on a portion of said path;

the improvement wherein said analyzer further includes capping means for blocking air access to the dispensing end of the pipette to prevent evaporation of liquid, and means for movably mounting said capping means within said path, said mounting means being constructed to allow said capping means to move from a first position that blocks said path and covers said pipette dispensing end, to a second position that unblocks said path and uncovers said pipette dispensing end;

said mounting means being further constructed to permit a test element advancing along said path to push said capping means into said second position, and further including a test element support below said pipette-positioning means for positioning a test element to receive liquid from said pipette, wherein said mounting means are pivotally attached to said test element support.

2. An analyzer as defined in claim 1, wherein said mounting means are spring-biased to urge said capping means into said first position.

3. In an analyzer for assaying an analyte of a body liquid dispensed onto a test element, the analyzer including means for guiding a test element along a predetermined path and support means adjacent said path for positioning and supporting a pipette to dispense a patient sample on a test element positioned on a liquid-dispensing portion of said path;

the improvement wherein said analyzer further includes housing means adjacent to said support means for blocking air access to the dispensing end of the pipette to prevent evaporation of liquid from the pipette, said housing means comprising,
  (a) means for providing a shroud, said shroud having a sufficient length so as to extend beyond the dispensing end of the pipette so as to provide an end surface on the shroud that is spaced from the pipette dispensing end,
  (b) capping means for contacting said shroud end surface, but not the pipette dispensing end, and for closing off air access to the pipette dispensing end through the shroud, and
  (c) mounting means for movably mounting said capping means between a first position and a second position, said first position being that in which said capping means contact said shroud end surface and said second position being that in which said capping means uncover said shroud end surface and any pipette dispensing end inside said shroud.

4. An analyzer as defined in claim 3, wherein said mounting means is constructed to move between said first and second positions in response to a test element advancing along said path to said liquid-dispensing portion of said path.

5. An analyzer as defined in claim 4, wherein said mounting means are spring-biased to urge said capping means into said first position in the absence of a test element at said liquid-dispensing portion of said path.

* * * * *